United States Patent [19]
Hunkapiller et al.

[11] Patent Number: 5,942,609
[45] Date of Patent: Aug. 24, 1999

[54] LIGATION ASSEMBLY AND DETECTION OF POLYNUCLEOTIDES ON SOLID-SUPPORT

[75] Inventors: Michael W. Hunkapiller, San Carlos; Andrew C. Hiatt, San Diego, both of Calif.

[73] Assignee: The Porkin-Elmer Corporation, Foster City, Calif.

[21] Appl. No.: 09/191,390

[22] Filed: Nov. 12, 1998

[51] Int. Cl.[6] .................................................. C07H 21/00
[52] U.S. Cl. .......................... 536/25.3; 435/6; 435/91.2; 436/501; 935/77; 935/78
[58] Field of Search ............... 435/6, 810, 91.2; 436/501; 935/77, 78; 536/25.3

[56] References Cited

U.S. PATENT DOCUMENTS

| | | | |
|---|---|---|---|
| 4,683,195 | 7/1987 | Mullis et al. .................................. | 435/6 |
| 5,093,251 | 3/1992 | Richards et al. ...................... | 435/172.3 |
| 5,158,877 | 10/1992 | Edwards et al. ........................... | 435/91 |
| 5,470,724 | 11/1995 | Ahern ....................................... | 435/91.2 |
| 5,503,995 | 4/1996 | Khudyakov et al. ................... | 435/91.1 |

FOREIGN PATENT DOCUMENTS

| | | | | |
|---|---|---|---|---|
| 4-262799 | 9/1992 | Japan | ................................ | C12Q 1/68 |
| 4-304900 | 10/1992 | Japan | ................................ | C12Q 1/68 |
| WO90/00626 | 1/1990 | WIPO | ............................ | C12Q 01/68 |

*Primary Examiner*—Ardin H. Marschel
*Attorney, Agent, or Firm*—Paul D. Grossman

[57] ABSTRACT

The present invention concerns methods of assembly of a polynucleotide on a solid-support by performing steps of annealing, ligation, and extension. The steps may be repeated in a cyclical manner to assemble immobilized double- or single-stranded polynucleotides with functional gene properties. The immobilized polynucleotides may be amplified by the polymerase chain reaction, and detected and quantitated by an exonuclease assay with a self-quenching, fluorescent probe. The polynucleotide may be cleaved from the solid-support by chemical or enzymatic cleavage.

22 Claims, 9 Drawing Sheets

FAM

TET

HEX

JOE

LIGATION ASSEMBLY AND DETECTION OF POLYNUCLEOTIDES ON SOLID-SUPPORT

FIELD OF THE INVENTION

The present invention relates generally to methods for assembly, analysis, detection, and cleavage of polynucleotides on a solid-support by annealing, ligation, and extension steps.

REFERENCES

Agarwal, K., Buchi, H., Caruthers, M., Gupta, N., Khorana, H., Kleppe, K., Kumar, A., Ohtsuka, E., Raj Bhandary U., van de Sande, J., Sgaramella, V., Weber, H., Yamada, T., (1970) "Total synthesis of the gene for an alanine transfer ribonucleic acid from yeast" Nature 227:27–34.

Andrus, A., McCollum, C. and Zon, G., "Automated system for polynucleotide synthesis and purification", U.S. Pat. No. 5,262,530, issued Nov. 16, 1993.

Aono, T. and Takada, H. Japan Application No. Hei 3(1991)-46, 193, Kokai Patent No. Hei 4(1992)-262,799, "A method of detecting a nucleic acid sequence and a reagent kit for this detection method", App. Date: Feb. 18, 1991, Pub. Date: Sep. 18, 1992.

Aono, T., Takada, H., Shibata, H., Japan Application No. Hei 3(1991)-93260, Kokai Patent No. Hei 4(1992)-304,900, "Method of detecting a target nucleic acid sequence and a reagent kit for this detection method", App. Date: Mar. 29, 1991, Pub. Date: Oct. 28, 1992.

Beaucage, S. and Caruthers, M. "Phosphoramidite compounds and processes" U.S. Pat. No. 4,415,732, issued Nov. 15, 1983.

Beaucage, S. and Iyer, R. (1992) "Advances in the synthesis of oligonucleotides by the phosphoramidite approach", Tetrahedron 48:2223–2311.

Beaucage, S. and Iyer, R. (1993) "The functionalization of oligonucleotides via phosphoramidite derivatives", Tetrahedron 49:1925–63.

Berger, S. and Kimmel, A. (1987) "Guide to Molecular Cloning Techniques" in Methods in Enzymology, Vol. 152, Ed. J. Abelson and M. Simon, Academic Press, Inc., San Diego.

Blackburn, M. and Gait, M. (1996) in Nucleic Acids in Chemistry and Biology, Oxford University Press, Oxford, pp. 132–33, 481–2.

Caruthers, M. and Beaucage, S., "Phosphoramidite compounds and processes" U.S. Pat. No. 4,415,732, issued Nov. 15, 1983.

Caruthers, M. and Matteucci, M., "Process for preparing polynucleotides" U.S. Pat. No. 4,458,066, issued 1984.

Clegg, R., (1992) "Fluorescence resonance energy transfer and nucleic acids", Meth. Enzymol. 211:353–388.

Goodchild, J. (1990) "Conjugates of oligonucleotides and modified oligonucleotides: A review of their synthesis and properties" Bioconjugate Chem. 1: 165–87.

Grossman, P., Bloch, W., Brinson, E., Chang, C., Eggerding, F., Fung, S., Iovannisci, D., Woo, S. and Winn-Deen, E. (1994) "High-density multiplex detection of nucleic acid sequences: oligonucleotide ligation assay and sequence-coded separation" Nucl. Acids Res. 22:4527–34.

Hermanson, G. (1996) "Nucleic acid and oligonucleotide modification and conjugation" in Bioconjugate Techniques, Academic Press, Inc., San Diego, pp. 639–71.

Holland, P. M., Abramson, R., Watson, R. and Gelfand, D. (1991) "Detection of specific polymerase chain reaction product by utilizing the 5' to 3' exonuclease activity of Thermus aquaticus DNA polymerase" Proc. Natl. Acad. Sci. 88:7276–80.

Horn, T. and Urdea, M., (1986) "A chemical 5'-phosphorylation of oligodeoxyribonucleotides that can be monitored by trityl cation release" Tetrahedron Lett. 27: 4705–08.

Khorana, H. (1979) "Total synthesis of a gene" Science, 203:614–25.

Lee, L. G., Connell, C., and Bloch, W. (1993) "Allelic discrimination by nick-translation PCR with fluorogenic probes" Nucl. Acids Res. 21:3761–66.

Livak, K., Flood, S., Marmaro, J., Giusti, W., and Deetz, K. (1995) "Oligonucleotides with fluorescent dyes at opposite ends provide a quenched probe system useful for detecting PCR product and nucleic acid hybridization" PCR Methods and Applications 4:357–362.

Livak, K., Flood, S. and Marmaro, J. "Method for detecting nucleic acid amplification using self-quenching fluorescence probe", U.S. Pat. No. 5,538,848, issued Jul. 23, 1996.

Livak, K., Flood, S., Marmaro, J. and Mullah, B. "Self-quenching fluorescence probe", U.S. Pat. No. 5,723,591, issued Mar. 3, 1998.

Menchen etal "4,7-Dichlorofluorescein dyes as molecular probes", U.S. Pat. No. 5,188,934, issued Feb. 23, 1993.

Mullah B. and Andrus, A. (1997) "Automated synthesis of double dye-labeled oligonucleotides using tetramethylrhodamine (TAMRA) solid supports" Tetrahedron Letters 38:5751–5754.

Mullah, B., Livak, K., Andrus, A. and Kenney, P. (1998) "Efficient synthesis of double dye-labeled oligodeoxyribonucleotide probes and their application in a real time PCR assay" Nucl. Acids Res. 26:1026–1031.

Sambrook, J., Fritsch, E. F., Maniatis, T., Eds. (1989) in Molecular Cloning, A Laboratory Manual, 2nd Ed., Volume II, Cold Spring Harbor, N.Y.

Shabarova, Z., Merenkova, I., Oretskaya, T., Sokolova, N., Skripkin, E, Alexeyeva, E., Balakin, A. and Bogdanov, A. (1991) "Chemical ligation of DNA: the first non-enzymatic assembly of a biologically active gene" Nucl. Acids Res. 19:4247–51.

Stamm, S. and Brosius, J. (1995) "Solid phase PCR" in PCR 2, A Practical Approach, IRL Press at Oxford University Press, Ed. M. McPherson, B. Hames, and G. Taylor, Oxford, U.K., p. 55–70.

Tyagi, S. and Kramer, F. R. (1996) "Molecular Beacons: Probes that fluoresce upon hybridization", Nature BioTechnology, 14:303–08.

Tyagi, S. and Kramer, F. R., "Detection probes, kits, and assays" WO 97/39008, Intl. Publ. Date Oct. 23, 1997.

BACKGROUND

The manipulation of functional gene sequences is the basis of molecular cloning. Ready availability of synthetic genes at a reasonable cost will accelerate the transformation of gene sequence information into gene function information. Deliberately-designed and unique-sequence synthetic genes will provide a stimulus to gene expression studies by making mutant proteins more available for study.

The classic method of de novo gene synthesis entails sequential annealing (hybridization) and ligation of the component synthetic oligonucleotides, a few at a time, in a homogeneous aqueous solution (Khorana, 1979; Blackburn, 1996). In this method, a mixture of overlapping, complementary oligonucleotides are annealed under conditions that favor formation of a correct double-stranded fragment (duplex DNA) with strand interruptions (nicks) at adjacent positions along the two strands. The resultant construct is then isolated and submitted to subsequent rounds of annealing, ligation, and isolation. The method requires efficient, rapid, and specific hybridization, the chemical synthesis of all the components of the gene, and many analytical and purification operations.

Purification of the intermediate duplex fragments after annealing and ligation is often complicated and ineffective in removing all misaligned, truncated, and otherwise imperfect constructs. Additionally, optimum hybridization of all duplex fragments and oligonucleotides is dependent on expert selection of the oligonucleotides within the gene. While the resulting double-stranded polynucleotide can be prepared up to several kilobases in length, the yield is typically less than 1% and the synthetic gene constructs have severely diminished biological activity relative to native genes when measured by protein expression levels (Agarwal, 1970).

Limitations to the classic method of gene synthesis include the known imperfections in chemical oligonucleotide synthesis, especially long oligonucleotides, resulting in impurities resulting from (i) failed-to-couple, truncated sequences, (ii) nucleobase-modified sequences, (iii) incompletely deprotected sequences, and (iv) other nucleotidic and non-nucleotidic by-products. Hybridization of impure oligonucleotide mixtures can lead to mismatches and impaired hybridization and ligation efficiency. The net result is low yields of functional, correct sequence oligonucleotides for use in synthetic gene assembly. An efficient method for the rapid and economical assembly of polynucleotides, i.e. genes or gene fragments, is desirable.

SUMMARY

The present invention is directed towards novel methods for assembly and detection of a polynucleotide on a solid-support. The methods are directed to rapid, efficient, low-cost, and large-scale synthesis of polynucleotides for use, for example, as synthetic genes for recombinant protein expression, as probes for diagnostic assays, or antisense therapeutic agents. The resulting polynucleotides on solid-support can be (i) amplified by the polymerase chain reaction (PCR), (ii) quantitated and detected by fluorescence-based, hybridization and exonuclease assays, (iii) manipulated for useful purposes while attached to the solid-support, or (iv) cleaved from the solid-support.

In a first aspect, the present invention comprises a method of synthesis of a polynucleotide on a solid-support where the method includes steps of annealing oligonucleotides to an immobilized oligonucleotide on a solid-support, ligating nick sites and extending portions of the polynucleotide to generate double-stranded polynucleotides on a solid-support.

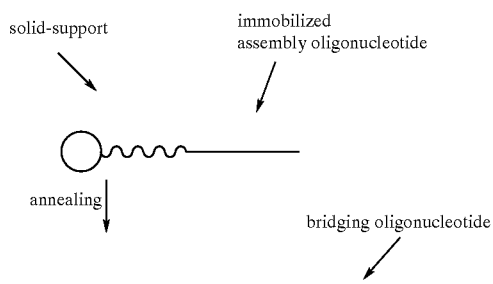

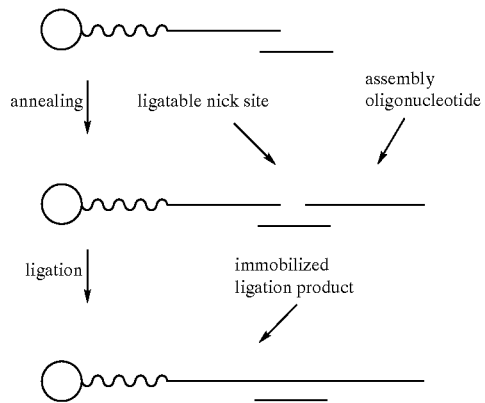

The first end of an oligonucleotide is immobilized on a solid-support. The non-immobilized end bears a phosphate group. One or more bridging oligonucleotides and two or more assembly oligonucleotides are annealed to the immobilized oligonucleotide such that a ligatable nick is formed between adjacent assembly oligonucleotides.

The nick sites are ligated thereby forming an immobilized ligation product. A primer is annealed to the immobilized ligation product and extended to create a double-stranded polynucleotide. The annealing and ligation steps may be repeated enough times to assemble the designed, immobilized double-stranded polynucleotide. Various combinations of assembly and bridging oligonucleotides for the assembly of polynucleotides a re illustrated in FIGS. 1–6.

A bridging oligonucleotide anneals to the immobilized oligonucleotide, whereby the bridging oligonucleotide is complementary to the non-immobilized end of the immobilized oligonucleotide and creates a first double-stranded fragment with an overhang. An assembly oligonucleotide, typically longer than the bridging oligonucleotide and complementary to the overhang of the non-immobilized strand, anneals at a nucleotide adjacent to the non-immobilized end of the immobilized oligonucleotide to create a second double-stranded fragment having a nick site and an overhang. Additional assembly and bridging oligonucleotides are introduced and anneal to form nicks in the immobilized strand and gaps in the non-immobilized strand. The nick sites are ligated in the immobilized strand by DNA ligase or by chemical ligation means. The non-immobilized strand is extended by polymerase, and primer, and nucleotide 5' triphosphates to create a double-stranded polynucleotide.

A second aspect of the present invention provides methods to detect and quantitate the assembled, double-stranded polynucleotide on the solid-support by fluorescent hybridization assay. The method further comprises annealing a self-quenching, fluorescence probe including reporter and quencher moieties and complementary to said polynucleotide after synthesis is completed. The probe may be comprised of nucleotides near the 5' terminus which are substantially complementary to the nucleotides near the 3' terminus whereby the unannealed probe exists in a quenched state. Upon annealing of the probe to the polynucleotide, the quenching A third aspect of the present invention provides methods to amplify the double-stranded polynucleotide on a solid-support by the polymerase chain reaction (PCR)

A fourth aspect of the present invention provides methods to detect and quantitate the product of the polymerase chain reaction by the fluorescence based, exonuclease assay (Lee, 1993; Holland, 1991).

A fifth aspect of the present invention provides methods to cleave the immobilized single-stranded polynucleotide from the solid-phase into solution by chemical or restriction enzyme cutting.

A device can be constructed to synthesize a polynucleotide on a solid-support by automating the steps of annealing, ligation, and primer extension in a cyclical manner. Liquid reagents can be delivered from vessels to the solid-supports under microprocessor control according to a program.

Certain aspects and embodiments of the present invention obviate many of the limitations and imperfections of the classic method (Khorana, 1979) of gene synthesis and confer some or all of the following advantages:

1) The solid support serves to allow efficient washing and removal of excess and non-annealed oligonucleotides, by-products, reagents, and contaminants. Purifications prior to the completion of gene assembly are not necessary.
2) DNA ligase requires absolute specificity during ligation and provides a proof reading advantage, i.e. the correct ligation product.
3) DNA polymerase also requires perfect complementarity at the point of extension and also provides a proofreading advantage, i.e. the correct extension product.
4) Extension of the non-immobilized strand requires only a portion of the eventual gene to be constructed with synthetic oligonucleotides.
5) The synthetic oligonucleotides can be relatively short, therefore they will be inexpensive, highly pure, and readily available.
6) Further experiments can be conducted on the assembled polynucleotide while immobilized on the solid-support.

DEFINITIONS

Figure 1:
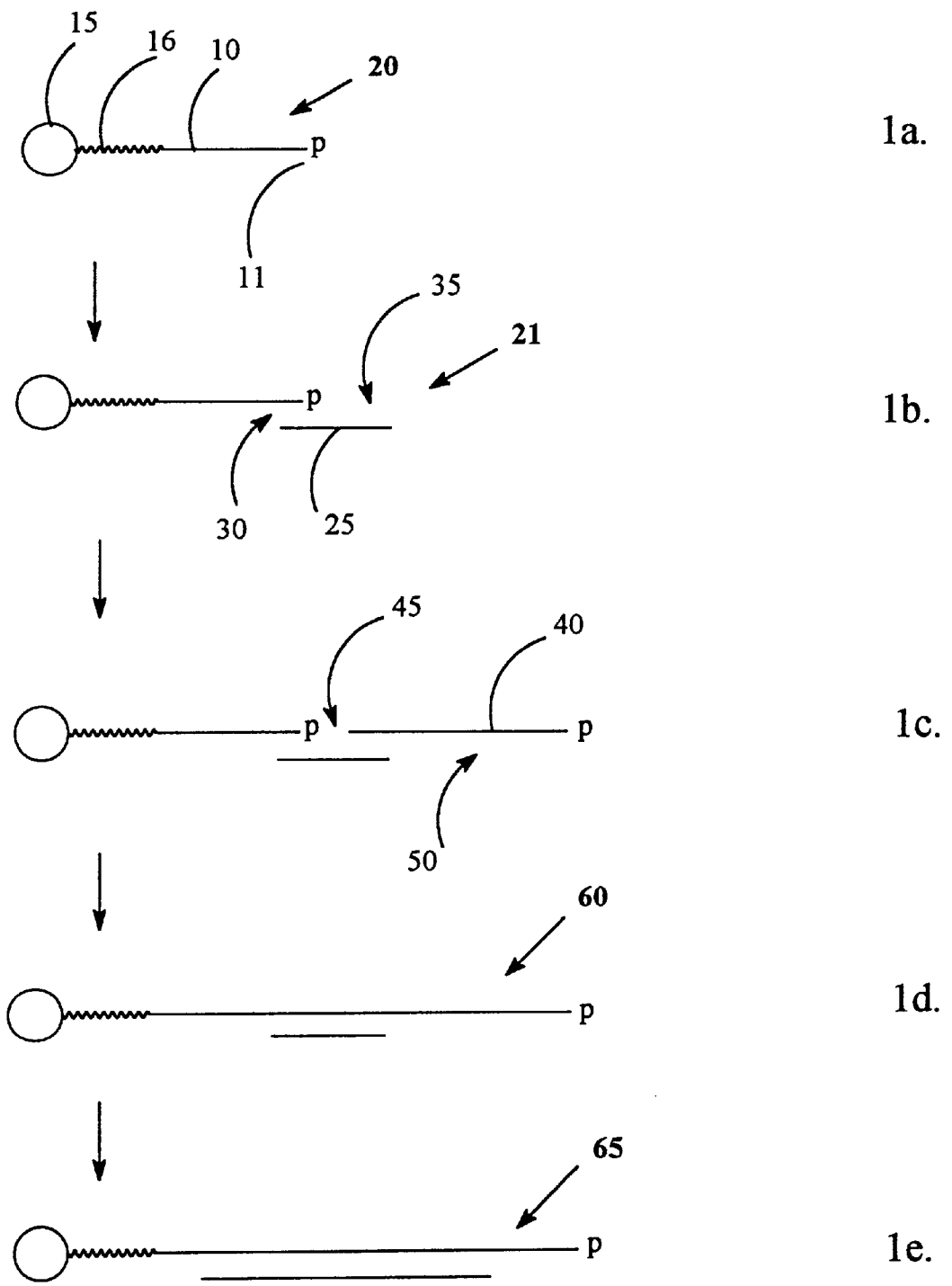
FIG. 1 shows sequential annealing to an immobilized, terminally phosphorylated assembly oligonucleotide 20 (1a) of a bridging oligonucleotide 25 (1b), followed by an assembly oligonucleotide 40, creating a nick 45 in the immobilized strand (1c), ligating the nick to form immobilized ligation product 60 (1d), and extending with polymerase (1e) to synthesize an immobilized double-stranded polynucleotide 65.

Unless stated otherwise, the following terms and phrases as used herein are intended to have the following meanings:

"Polynucleotide" or "oligonucleotide" refer to linear polymers of natural nucleotide monomers or analogs thereof, including double and single-stranded deoxyribonucleotides "DNA", ribonucleotides "RNA", α-anomeric forms thereof, and the like.

"Oligonucleotide analogs" are polymeric analogs of oligonucleotides made from monomeric nucleotide analog units, and possessing some of the qualities and properties associated with nucleic acids.

"Nucleotide" is the monomer unit in biopolymer nucleic acids, such as DNA or RNA, abbreviated as "nt". A nucleotide is composed of three moieties: sugar, phosphate, and nucleobase (Blackburn, 1996). When part of a duplex, nucleotides are also referred to as "bases" or "base pairs", abbreviated as "bp". The most common naturally-occurring nucleobases, adenine (A), guanine (G), uracil (U), cytosine (C, and thymine (T) bear the hydrogen-bonding functionality that binds one polynucleotide strand to another in a sequence specific manner. "Nucleoside" refers to a nucleotide that lacks a phosphate. Usually the nucleoside monomers are linked by "phosphodiester linkages", where as used herein, refer to phosphodiester bonds or bonds including phosphate analogs thereof, including associated counterions, e.g., $H^+$, $NH_4^+$, $Na^+$, and the like. Polynucleotides typically range in size from a few monomeric units, e.g. 8–40 nt, to several thousand monomeric units. Most molecular biology applications for polynucleotides require unique sequences of 15–30 nt. Whenever a DNA polynucleotide is represented by a sequence of letters, such as "ATGCCTG," it will be understood that the nucleotides are in 5'→3' order from left to right. The ends of a single-strand oligonucleotide are referred to as the "5' terminus" and "3' terminus".

"Watson/Crick base-pairing" refers to the complementary pattern of specific pairs of nucleotides in DNA, RNA, and analogs thereof, that bind together through hydrogen-bonds, e.g. A pairs with T and U, and G pairs with C.

"Attachment site" refers to the atom on an oligonucleotide to which is attached a linker.

"Linker" refers to one or more atoms connecting an oligonucleotide to a solid-support, label, or other moiety.

The term "solid-support" refers to a material in the solid-phase that interacts with reagents in the liquid phase by heterogeneous reactions. Solid-supports can be derivatized with oligonucleotides by covalent or non-covalent bonding through one or more attachment sites, thereby "immobilizing" an oligonucleotide to the solid-support.

The term "annealing" is used synonymously with "hybridization" and refers to the Watson/Crick base-pairing interactions between two strands of oligonucleotides within a duplex.

The term "overhang" refers to a single-stranded terminus of a duplex of base-paired oligonucleotides. The overhang may be one or more bases in length and allows for annealing of a complementary oligonucleotide prior to ligation and extension during polynucleotide assembly.

"Denaturing" conditions or reagents disrupt base-pairing and cause separation of a duplex into single-strands. Denaturing conditions and reagents include heat, basic pH, high salt concentrations and specific denaturants, such as formamide and ammonium hydroxide. "Non-denaturing" conditions allow base-pairing in duplex structures to persist. Non-denaturing conditions typically include low temperature, neutral pH, low salt concentrations, neutral aqueous buffers, and reagents which do not disrupt hydrogen bonding between nucleobases.

The term "ligate" refers to the reaction of covalently joining adjacent oligonucleotides through formation of an internucleotide linkage.

The term "ligase" refers to a class of enzymes and their functions in forming a phosphodiester bond in adjacent oligonucleotides which are annealed to the same oligonucleotide. Particularly efficient ligation takes place when the terminal phosphate of one oligonucleotide and the terminal hydroxyl group of an adjacent second oligonucleotide are annealed together across from their complementary sequences within a double helix, i.e. where the ligation process ligates a "nick" at a ligatable nick site and creates a complementary duplex (Blackburn, 1996). The site between the adjacent oligonucleotides is referred to as the "ligatable nick site", "nick site", or "nick", whereby the phosphodiester bond is non-existent, or cleaved.

The intervening single-stranded portion between two oligonucleotides in a duplex is referred to as a "gap", consisting of one or more nucleotides. A gap can be eliminated or "filled in" by extension from a 3' terminus of a primer.

"Primer extension reaction", "extension", and "extending" refer to a reaction between a template/primer duplex, 5' triphosphate nucleotides (NTP), and a polymerase which results in the addition of the nucleotide to a 3'-end of the primer such that the added nucleotides are complementary to the corresponding nucleotides of the template nucleic acid.

"Label" refers to a group attached to an oligonucleotide. The label is capable of conducting a function such as giving a signal for detection of the molecule by such means as fluorescence, chemiluminescence, and electrochemical luminescence (Hermanson, 1996). Alternatively, the label allows for separation or immobilization of the molecule by a specific or non-specific capture method (Andrus, 1995).

"Primer" refers to an oligonucleotide capable of selectively annealing to a specified target nucleic acid and thereafter serving as a point of initiation of a primer extension reaction wherein the primer is extended in a 5'→3' direction.

The term "5'→3' nuclease activity" refers to an enzyme activity that cleaves nucleic acid at phosphodiester bonds. This activity can be either endo (cleaves at internal phosphodiester bonds) or exo (cleaves at the phosphodiester bond closest to either the 5' or 3' terminus of the nucleic acid strand.

The term "self-quenching" refers to an intermolecular, fluorescence energy transfer effect, e.g. a reporter and quencher are joined on an oligonucleotide in a configuration that permits energy transfer from the reporter to the quencher.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

I. Synthesis of Assembly and Bridging Oligonucleotides

Generally, the design and synthesis of bridging and assembly oligonucleotides of the invention follows conventional teachings Beaucage, 1992; Caruthers, 1983). The phosphoramidite method of oligonucleotide synthesis (Beaucage, 1983; Beaucage, 1992) is the universally favored method of preparing the oligonucleotides used in the invention. The phosphoramidite method is a highly refined chemical operation of cyclical addition of nucleotide monomer units to a chain of DNA growing on a solid-support and is usually practiced using automated, commercially available, synthesizers, which function as microprocessor-controlled, reagent delivery robots, e.g. ABI 391, 392, 394, and 3948 DNA/RNA Synthesizers (Perkin-Elmer Corp) (Caruthers, 1984). The 5' or 3' terminus of an oligonucleotide can be phosphorylated with a phosphoramidite reagent (Horn, 1986) or enzymatically with polynucleotide kinase and ATP (Berger, 1987, p. 438–39).

Oligonucleotides may immobilized on solid supports through any one of a variety of well-known covalent linkages or non-covalent interactions. The support is comprised of insoluble materials, preferably having a rigid or semirigid character, and may be any shape, e.g. spherical, as in beads, rectangular, irregular particles, resins, gels, microspheres, or substantially flat. In some embodiments, it may be desirable to create an array of physically separate synthesis regions on the support with, for example, wells, raised regions, dimples, pins, trenches, rods, pins, inner or outer walls of cylinders, and the like.

Preferred support materials include agarose, polyacrylamide, magnetic beads (Stamm, 1995), polystyrene (Andrus, 1993), controlled-pore-glass (Caruthers, 1984), polyacrylate, hydroxethylmethacrylate, polyamide, polyethylene, polyethyleneoxy, or copolymers and grafts of such. Polyethyleneoxy/polystyrene co-polymer is used extensively for small molecule and peptide synthesis and is a particularly preferred solid support of the present invention (Tentagel, Rapp Polymere, Tubingen, Germany). The hydrophilic nature of the polyethyleneoxy groups promotes rapid kinetics and binding when aqueous solvents are used. Other embodiments of solid-supports include small particles, membranes, frits, non-porous surfaces, addressable arrays, vectors, plasmids, or polynucleotide-immobilizing media.

As used in the methods of the present invention, oligonucleotides are attached by covalent bonds, ionic bonds, or other affinity interactions, to chemically reactive functionality on the solid-supports. Oligonucleotides can be attached to solid-supports at their 3', 5', sugar, or nucleobase sites (Goodchild, 1990; Beaucage, 1993). The 3' site for attachment via a linker to the support is preferred due to oligonucleotide synthesis ease and efficiency, and due to the many options available for stable or selectively cleavable linkers (Beaucage, 1992). In this manner, gram to kilogram scale preparations of immobilized oligonucleotides can be obtained at loading ranges of 1–2000 nmoles oligonucleotide per gram of support, and preferably in a range of 500–1000 nmoles oligonucleotide per gram of support.

Immobilization is preferably accomplished by a covalent linkage between the support and the oligonucleotide. The linkage unit, or linker, is designed to be stable and facilitate accessibility of the immobilized nucleic acid to its sequence complement. Alternatively, non-covalent linkages such as between biotin and avidin or stepavidin are useful. A typical method for attaching oligonucleotides is coupling a thiol functionalized polystyrene bead with a 3' thiol-oligonucleotide under mild oxidizing conditions to form a disulfide linker. Examples of other functional group linkers include ester, amide, carbamate, urea, sulfonate, ether, and thioester.

A 5' or 3' biotinylated oligonucleotide can be immobilized on avidin or strepavidin bound to a support such as glass or SEPHAROSE™ (Pharmacia Biotech).

Alternatively the 5' terminus of an oligonucleotide can be immobilized to a solid-support. The directionality of the assembled polynucleotide and the component oligonucleotides of the preceding embodiments would thus be reversed, although equally accommodated and efficient.

II. Annealing, Ligation, and Extension

Annealing

Oligonucleotides are preferably annealed for assembly in aqueous media which promotes Watson/Crick base-pairing, at or near room temperature. Exemplary annealing conditions are a temperature range of 30–65° C. and an assembly solvent of 0.2–1.0 M NaCl or KCl, 10–50 mM $MgCl_2$, 100 mM Tris-HCl and 0–50% formamide, at pH=7–9 (Berger, 1987, p. 549). For example, 1 mg of support, (1 nmole, loaded at 1 μmole oligonucleotide/gm) is annealed with 5 nmole of each oligonucleotide during each annealing and ligation cycle, in a total volume of 10–50 μl solution.

Ligation

In a ligation reaction, a ligation reagent effects ligation of a ligatable nick site located between two assembly oligonucleotides. DNA ligase conducts enzymatic ligation upon a ligatable nick site to create an internucleotide phosphodiester bond and create a continuous strand in the immobilized ligation product. Ligation with DNA ligase is highly specific and generally occurs only with perfect complementarity close to the nick site. With ATP or $NAD^+$, DNA ligase catalyzes the formation of a phosphodiester bond between the 5' phosphoryl terminus and the 3'-hydroxyl terminus of two, double-stranded oligonucleotides (Wu, 1987; Helfman, 1987; Grossman, 1994).

In a preferred embodiment of the present invention, the 5' phosphate group of an assembly oligonucleotide is ligated to the 3' hydroxyl of an adjacent assembly oligonucleotide. Typically the 5' terminus of the ligatable nick site is phosphorylated and the 3' terminus is hydroxyl, although the opposite orientation of 5' hydroxyl and 3' phosphate also leads to efficient ligation by DNA ligase (Sambrook, 1989, p. 5.61). Enzymatic ligation of the assembled polynucleotide on solid-support can be conducted by treating the assembled polynucleotide on solid-support (e.g. 1c., FIG. 1) e.g. with 20 mM dithreitol, 10 mM $MgCl_2$, 1 mM ATP, and 50 mM Tris-HCl, followed by the addition of T4 DNA ligase, or other forms of ligase. For example, 1 nmole of assembled polynucleotide would undergo ligation with 1 unit of ligase in a total volume of 10–50 μl solution (Aono, 1991). After several minutes to several hours at 37° C. with gentle agitation, the support is then filtered, centrifuged, or aspirated to remove excess liquid reagents, and washed with neutral aqueous buffer, such as several ml of 0.1 M triethylammonium acetate, pH 7.

A ligatable nick site of an assembled polynucleotide can also be chemically ligated with reagents, such as cyanogen bromide and dicyclohexylcarbodiimide, to form an internucleotide phosphate linkage between two adjacent assembled oligonucleotides, one of which bears a 5' or 3' phosphate group, annealed to a bridging oligonucleotide (Shabarova, 1991).

The solid-support may be washed under denaturing conditions after each ligation to remove the non-immobilized strands. Preferred denaturants include sodium hydroxide, ammonium hydroxide, formamide, urea, sodium chloride and sodium acetate.

Extension

Figure 6:
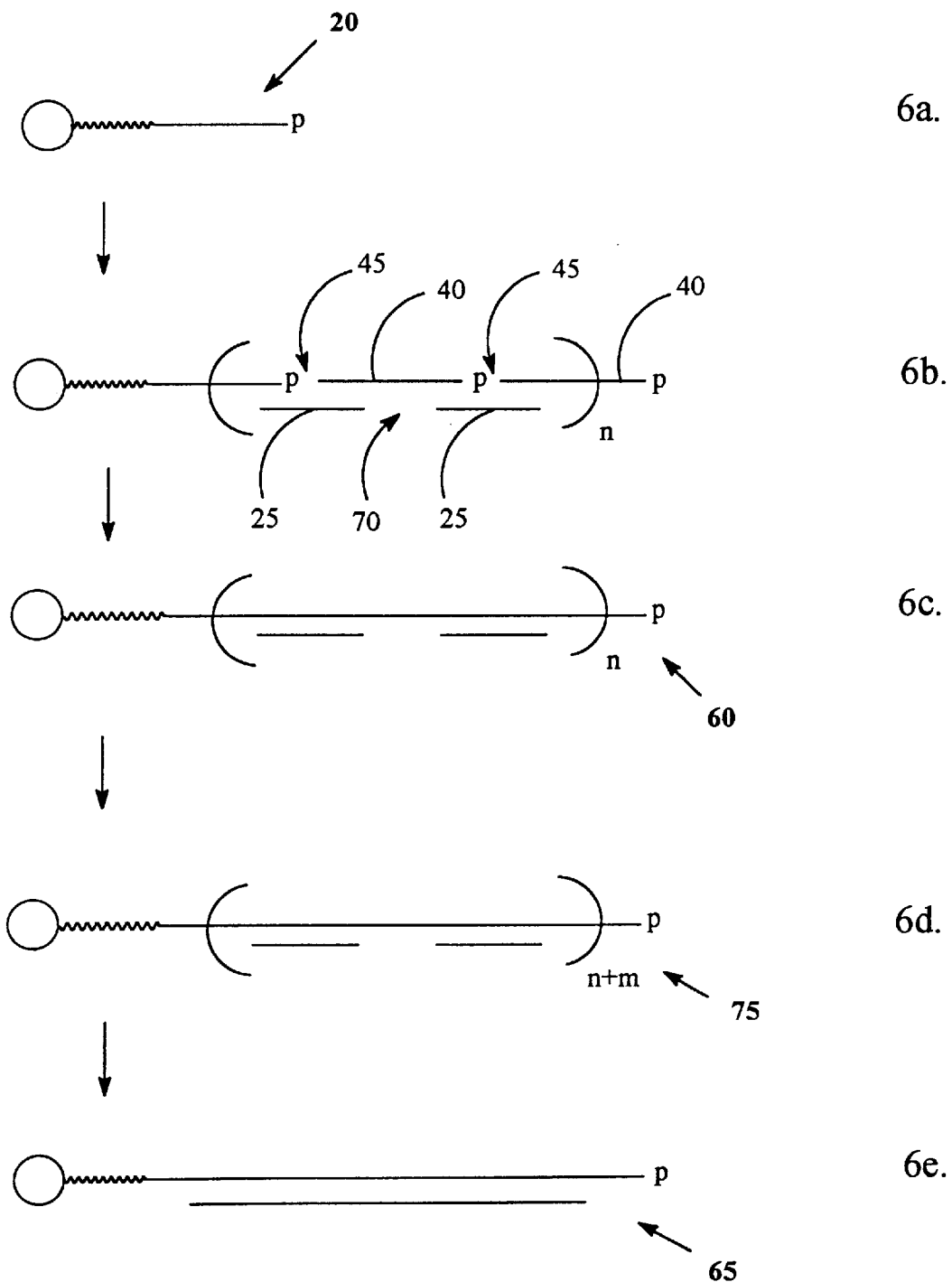
FIG. 6 shows concurrent annealing to an immobilized, terminally phosphorylated assembly oligonucleotide 20 (6a) of one or more bridging oligonucleotides 25 and two or assembly oligonucleotides 40, creating nicks 45 in the immobilized strand and gaps 70 in the non-immobilized strand (6b), ligating the nicks to form immobilized ligation product 60 (6c), repeating m times the steps of annealing and ligating (6d), and extending with polymerase to synthesize an immobilized double-stranded polynucleotide 65 (6e).

The repetitively annealed and ligated immobilized ligation product is copied with DNA polymerase, a primer, nucleotide 5' triphosphates, and other reagents necessary for extension to create a double-stranded polynucleotide on the solid-support (FIG. 6e.).

In a primer extension reaction, a primer complementary to the polynucleotide is annealed to the polynucleotide. A DNA polymerase catalyzes the sequential joining of complementary nucleotides from nucleotide 5'-triphosphates to the 3' terminus of the primer by formation of new internucleotide phosphate bonds. A new complementary strand of DNA is thus extended from the primer.

After completing the annealing and ligation cycles, immobilized strands of the assembled polynucleotide may be annealed to one or more bridging oligonucleotides, across from which the nick sites were ligated. The single stranded portions, or "gaps" of the assembled polynucleotide may be filled in by primer extension, followed by ligation of the nick. The 3' terminus within a gap in a duplex can be extended from the 3' terminus of a primer by a DNA polymerase, and 2'-deoxynucleotide-5'-triphosphates, under known conditions (Berger, 1987, p. 91–98). Polymerase enzymes suitable for use in the extension step of the synthesis methods of the invention or for use in the amplification of the polynucleotide by polymerase chain reaction include any that are capable of polymerizing nucleotide triphosphates from a polynucleotide immobilized to a solid-support. Preferred polymerase enzymes have high fidelity and processivity. Suitable enzymes include, but are not limited to, DNA Polymerase I, Klenow fragment of DNA Polymerase I, T7 DNA Polymerase, T4 Polymerase, Taq Polymerase, and AMV (or MULV) Reverse Transcriptase or closely homologous mutants (Sambrook, 1989, p. 5.35–56). More preferably, the enzyme for the extension step and the polymerase chain reaction is Taq Polymerase, or closely homologous mutant.

Alternatively, the non-immobilized strand and bridging oligonucleotides annealed to the immobilized strand can be removed from the immobilized ligation product under denaturing conditions. Primer extension with polymerase, a primer, and nucleotide 5' triphosphates can copy the immobilized strand from the priming site. The primer will extend at its 3' hydroxyl toward the 3' terminus of the immobilized strand.

Nucleotide 5' triphosphates (NTP) suitable for use in the extension step of the synthesis methods of the invention or for use in the amplification of the polynucleotide by polymerase chain reaction include any that are capable of being polymerized by a polymerase enzyme. Suitable NTPs include both naturally occurring and synthetic nucleotide triphosphates, and are not limited to, ATP, dATP, CTP, dCTP, GTP, dGTP, UTP, TTP, dUTP, 5-methyl-CTP, 5-methyl-dCTP, ITP, dITP, 2-amino-ATP, 2-amino-dATP, as well as the α-thiotriphosphates, 2'-O-methyl-ribonucleotide 5'-triphosphates 2'-fluoro-NTP, and 2'-amino-NTP for all of the above. Preferably, the nucleotide triphosphates used in the methods of invention are selected from the group consisting of dATP, dCTP, dGTP, TTP, and mixtures thereof Modified nucleobases can also be used, including but not limited to, 5-Br-UTP, 5-Br-dUTP, 5-F-TTP, 5-F-dUTP, 5-propynyl dCTP, and 5-propynyl-dUTP. Most of these nucleotide triphosphates are widely available from commercial sources such as Sigma Chemical Co., St. Louis, Mo. Nucleotide triphosphates are advantageously used in the methods of the present invention at least because they are generally cheaper than the phosphoramidite nucleoside monomers used in the chemical synthesis of oligonucleotides.

Alternatively, fluorescent-labelled dNTP can be added, or substituted for one or more of ATP, GTP, CTP, TTP, to incorporate fluorescent dyes into the double-stranded assembled polynucleotide product.

Typical conditions for primer extension can include the addition of the following solution (1–50 μl) to the assembled polynucleotide on solid support (50–1000 pmole) comprising: primer oligonucleotide (if required), 1 unit DNA polymerase, 80 mM Tris-HCl (pH 8.0), 10 mM dithiothreitol, 4 mM spermidine, 8 mM $MgCl_2$, 50 mM NaCl, 160 μg/ml BSA, 0.02% Triton X-100, and 2 mM each of ATP, GTP, CTP, TTP. For example, after 10 minutes to 2 hours at 37° C., excess liquid reagents are removed from the support and the support is washed with 0.5–5 ml of neutral aqueous buffer, such as 0.1 M triethylammonium acetate (Sambrook, 1989, p. 5.35–5.50.

III. Assembly of Polynucleotides

Several preferred embodiments of the invention are described here that illustrate the method of assembly of polynucleotides on a solid-support.

1. Sequential Annealing

In a first embodiment of the assembly method of the invention, an assembly oligonucleotide 10, preferably having a 5' phosphate group 11, is immobilized, e.g. 1–10 mg, 0.5–20 nmoles, to a solid support 15 through a linker 16 (1a, FIG. 1). The immobilized assembly oligonucleotide 20 is suspended in an assembly solvent, e.g. 0.2 M NaCl or KCl and 0–50% formamide. Aqueous assembly solvents which facilitate Watson/Crick base-pairing at or near room temperature are preferred. A bridging oligonucleotide 25, e.g. 2–10 fold molar excess, 1–200 nmoles, is added with a sequence at least partially complementary to the immobilized assembly oligonucleotide 20 under conditions favoring annealing of the bridging oligonucleotide to the immobilized assembly oligonucleotide 20 to form a hybrid 21 having a duplex region 30 and a first overhang 35 (1b.). Excess or non-annealed bridging oligonucleotide 25 and other impurities may be removed by washing the solid-support under non-denaturing conditions. An assembly oligonucleotide 40, e.g. 2–10 fold molar excess, 1–200 nmoles, having a sequence at least partially complementary to the first overhang 35 is added. Assembly oligonucleotide 40 anneals to overhang 35 of the bridging oligonucleotide 25 and adjacent to the immobilized oligonucleotide 10, creating a ligatable nick site 45 and a second overhang 50 (1c.).

A ligating agent, e.g. DNA ligase, ATP, and other reagents necessary for ligation, are added to ligate the immobilized assembly oligonucleotide 20, to the adjacent assembly oligonucleotide 40 to form an immobilized ligation product 60 (1d.).

A complement to the immobilized ligation product is then synthesized with DNA polymerase, a primer, nucleotide 5' triphosphates, and other reagents necessary for primer extension to create a double-stranded polynucleotide on the solid-support 65 (1e.).

2. Concurrent Annealing with two Oligonucleotides

Figure 2:
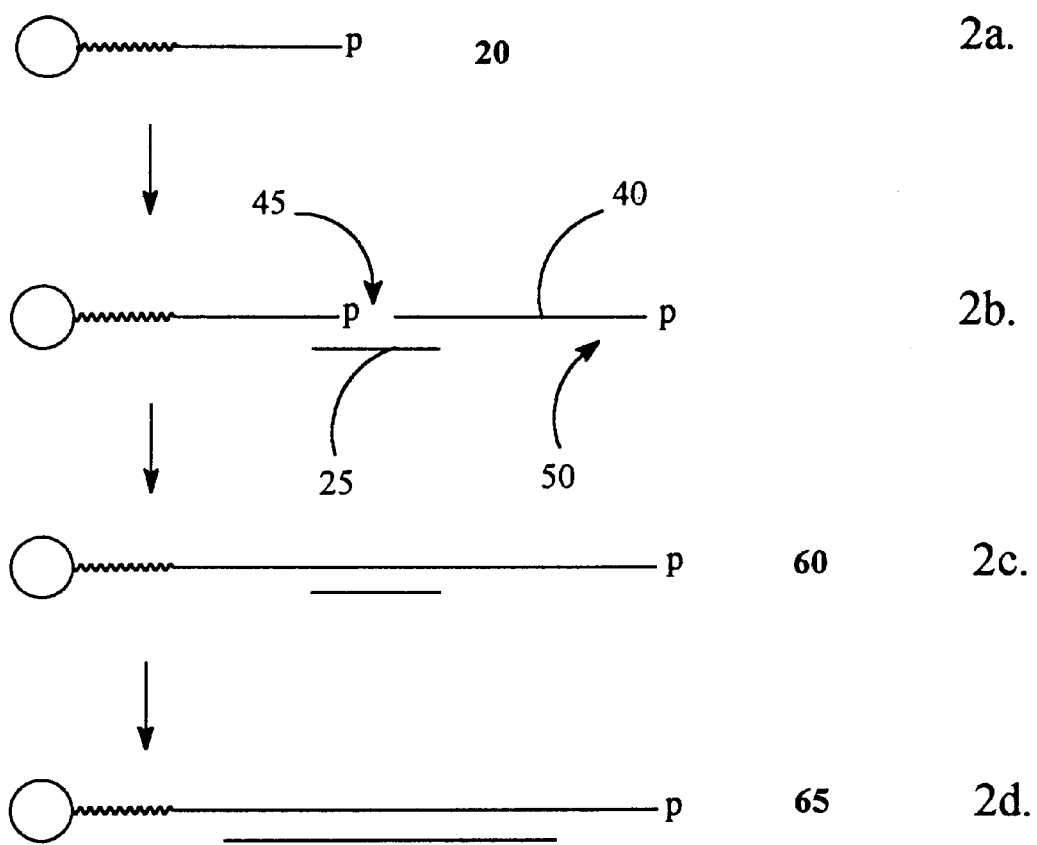
FIG. 2 shows concurrent annealing to an immobilized, terminally phosphorylated assembly oligonucleotide 20 (2a) of two oligonucleotides as a mixture, one bridging 25 and one assembly 40, creating a nick 45 in the immobilized strand (2b), ligating the nick to form immobilized ligation product 60 (2c), and extending with polymerase (2d) to synthesize an immobilized double-stranded polynucleotide 65.

In a second embodiment of the assembly method of the invention, an immobilized assembly oligonucleotide 20 (2a., FIG. 2) is suspended in an assembly solvent. A bridging oligonucleotide 25, with a sequence at least partially complementary to the immobilized oligonucleotide, and an assembly oligonucleotide 40, with a sequence at least partially complementary to the bridging oligonucleotide, are added as a mixture. The bridging oligonucleotide 25 anneals to the immobilized assembly oligonucleotide 20 and the assembly oligonucleotide 40 anneals adjacent to the immobilized assembly oligonucleotide 20, creating a ligatable nick site 45 and an overhang 50 (2b.). Excess or non-annealed oligonucleotides 25 and 40, and other impurities may be removed by washing under non-denaturing conditions.

A ligating agent, e.g. DNA ligase, ATP, and other reagents necessary for ligation are added to ligate the immobilized assembly oligonucleotide 20 to the adjacent assembly oligonucleotide 40 to form an immobilized ligation product 60 (2c.).

A complement to the immobilized ligation product is then synthesized with DNA polymerase, a primer, nucleotide 5' triphosphates, and other reagents necessary for primer extension to create a double-stranded polynucleotide on the solid-support 65 (2d.).

The preceding may be conducted in a similar manner and with similar quantities as section III.1.

3. Concurrent Annealing with more than Two Oligonucleotides

Figure 3:
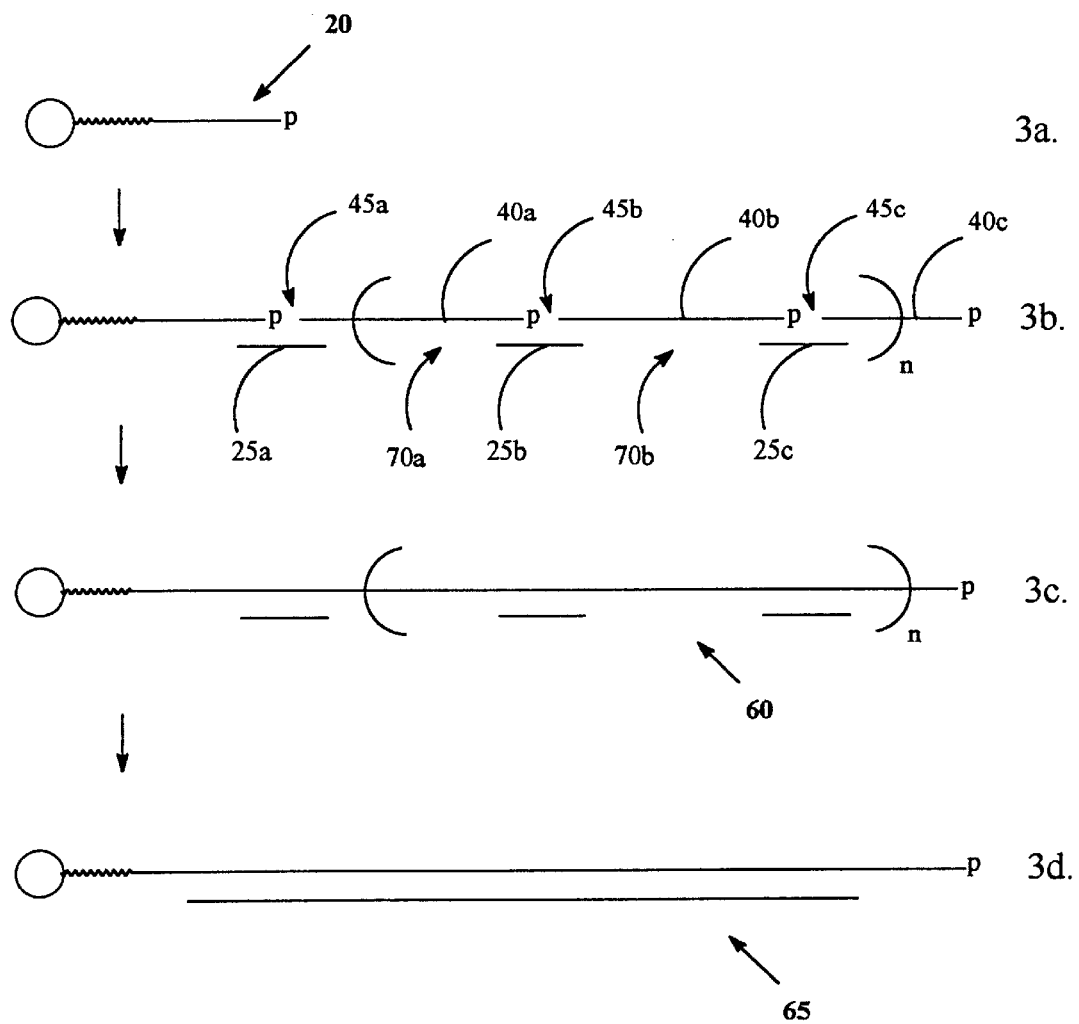
FIG. 3 shows concurrent annealing to an immobilized, terminally phosphorylated assembly oligonucleotide 20 (3a) of one or more bridging oligonucleotides 25 and two or assembly oligonucleotides 40, creating nicks 45 in the immobilized strand and gaps 70 in the non-immobilized strand (3b), ligating the nicks to form immobilized ligation product 60 (3c), and extending with polymerase (3d) to synthesize an immobilized double-stranded polynucleotide 65.
Figure 4:
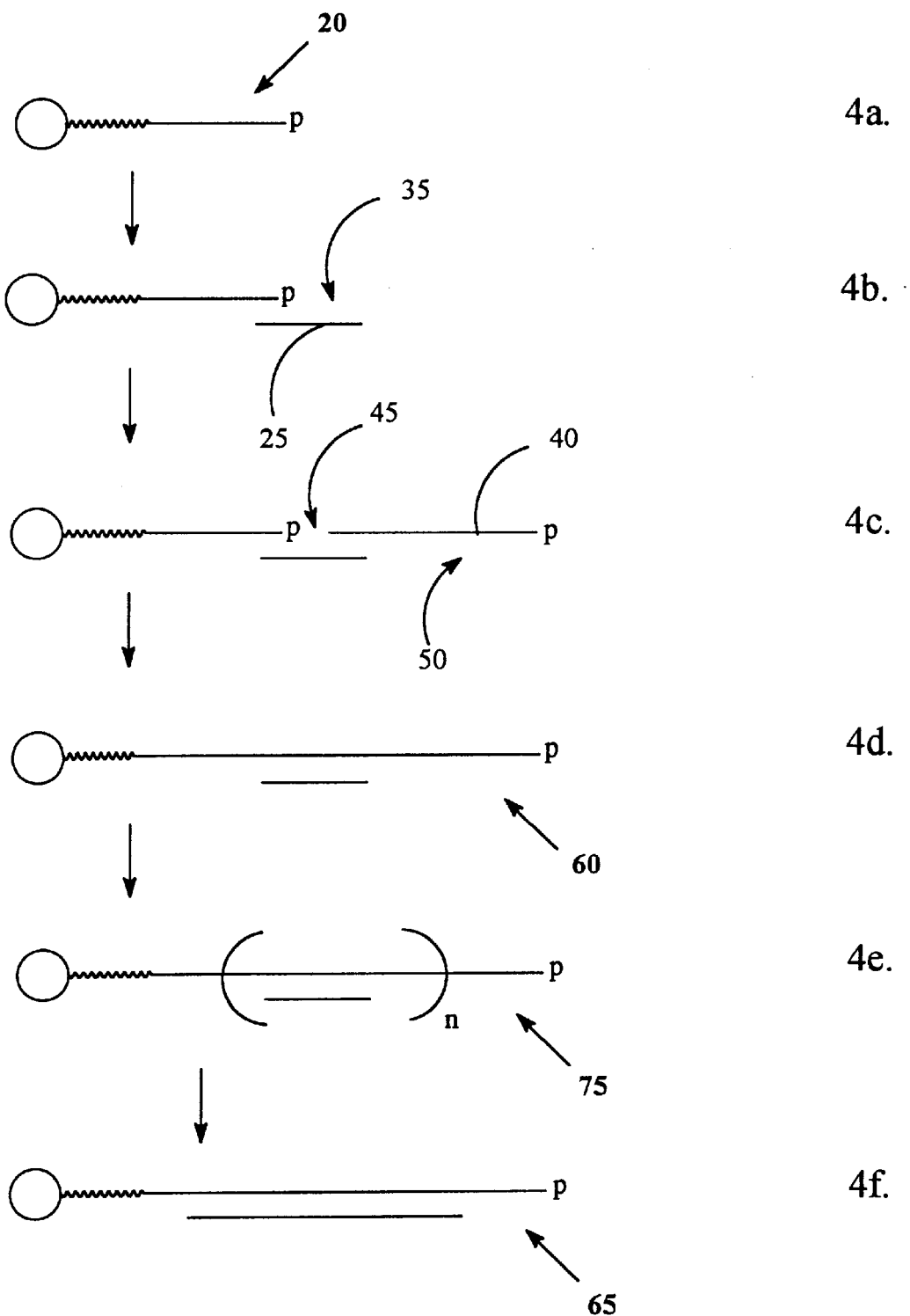
FIG. 4 shows sequential annealing to an immobilized, terminally phosphorylated assembly oligonucleotide 20 (4a) of a bridging oligonucleotide 25 (4b) followed by an assembly oligonucleotide 40, creating a nick 45 in the immobilized strand (4c), ligating the nick to form immobilized ligation product 60 (4d), repeating n times the steps of annealing and ligating (4e), and extending with polymerase (4f) to synthesize an immobilized double-stranded polynucleotide 65.
Figure 5:
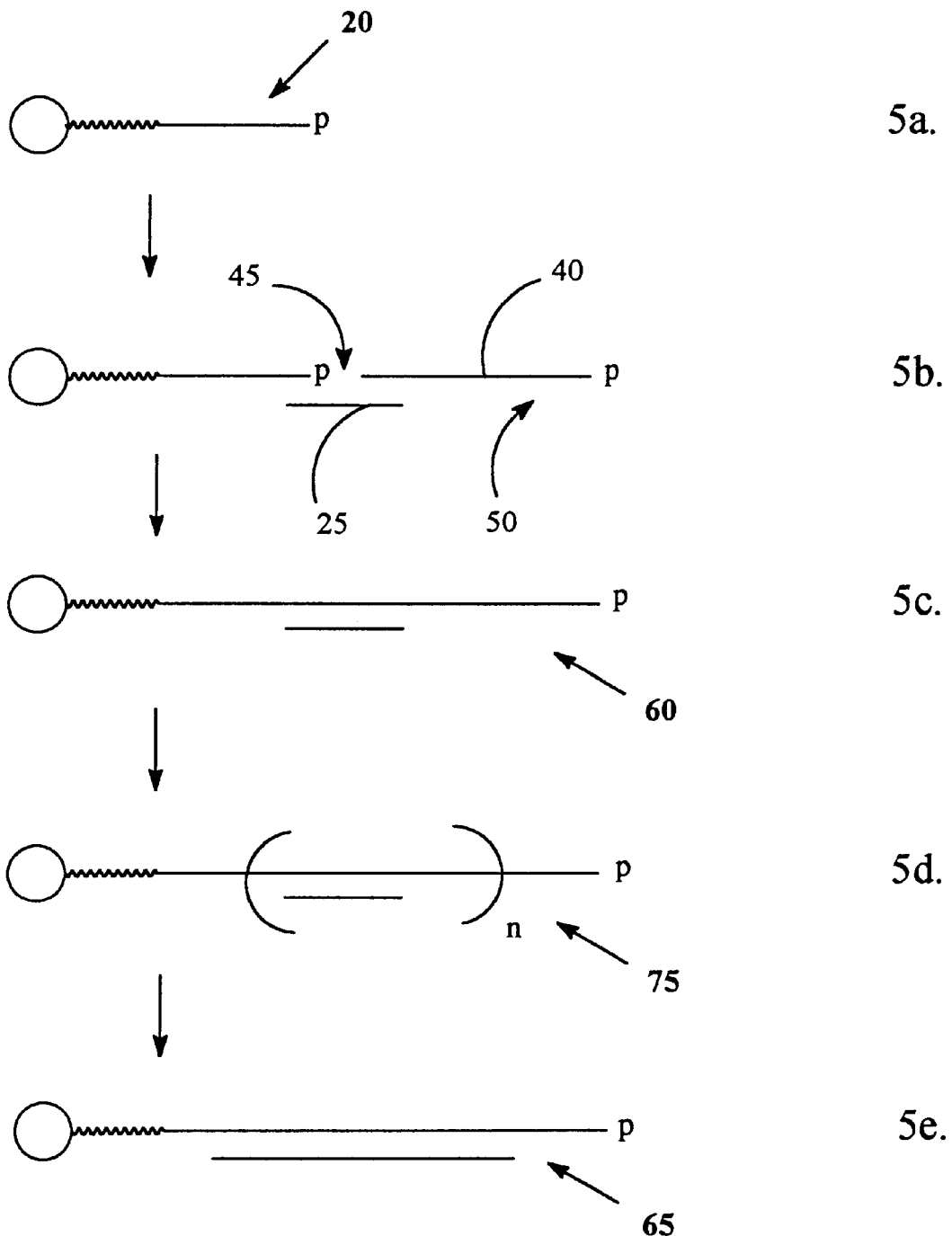
FIG. 5 shows concurrent annealing to an immobilized, terminally phosphorylated assembly oligonucleotide 20 (5a) of two oligonucleotides as a mixture, one bridging 25 and one assembly 40, creating a nick 45 in the immobilized strand (5b), ligating the nick to form immobilized ligation product 60 (5c), repeating n times the steps of annealing and ligating (5d), and extending with polymerase to synthesize an immobilized double-stranded polynucleotide 65 (5e).

In a third embodiment of the assembly method of the invention, an immobilized assembly oligonucleotide 20 (3a., FIG. 3) is suspended in an assembly solvent. More than two annealing oligonucleotides, e.g. 40a–c, are added as a mixture. The mixture contains one or more bridging oligonucleotides 25a–c which anneal to form gaps 70a–b and one or more assembly oligonucleotides 40a–c that anneal to form ligatable nick sites 45a–c (3b.). Excess or non-annealed oligonucleotides 25 and 40, and other impurities may be removed by washing under non-denaturing conditions.

A ligating agent, e.g. DNA ligase, ATP, and other reagents necessary for ligation are added to ligate the nick sites at adjacent assembly oligonucleotides to form an immobilized ligation product 60 (3c.).

A complement to the immobilized ligation product is then synthesized with DNA polymerase, a primer, nucleotide 5' triphosphates, and other reagents necessary for primer extension to create a double-stranded polynucleotide on the solid-support 65 (3d.).

The preceding may be conducted in a similar manner and with similar quantities as section III.1.

4. Repetitive Sequential Annealing

The steps of sequential annealing of a bridging and an assembly oligonucleotide, as described in section III.1, followed by ligation, and interspersed with washing steps may be repeated up to 100 times or more (4e.). The repetitively annealed and ligated immobilized ligation product 75 is copied with DNA polymerase, a primer, nucleotide 5' triphosphates, and other reagents necessary for extension to create an immobilized double-stranded polynucleotide on the solid-support 65 (4f.).

The preceding may be conducted in a similar manner and with similar quantities as section III.1.

5. Repetitive Concurrent Annealing with Two Oligonucleotides

The steps of concurrent annealing of a bridging and an assembly oligonucleotide, as described in section III.2, followed by ligation, and interspersed with washing steps may be repeated up to 100 times or more (5d.). The repetitively annealed and ligated immobilized ligation product 75 is copied with DNA polymerase, a primer, nucleotide 5' triphosphates, and other reagents necessary for extension to create an immobilized double-stranded polynucleotide on the solid-support 65 (5e.).

The preceding may be conducted in a similar manner and with similar quantities as section III.1.

6. Repetitive Concurrent Annealing with more than Two Oligonucleotides

The steps of concurrent annealing of more than one bridging oligonucleotide and more than one assembly oligonucleotide, followed by ligation, and interspersed with washing steps, as described in section III.3, may be repeated up to 100 times or more (6d.). The repetitively annealed and ligated immobilized ligation product 75 is copied with DNA polymerase, a primer, nucleotide 5' triphosphates, and other reagents necessary for extension to create an immobilized double-stranded polynucleotide on the solid-support 65 (6e.).

The preceding may be conducted in a similar manner and with similar quantities as section III.1.

IV. Design of Polynucleotide Assembly

A gene of known DNA sequence and of particular interest is selected for assembly. The size of the gene may range from 50 bp to 5000 bp or more. In planning, one strand of the polynucleotide sequence to be synthesized is divided into a contiguous set of assembly oligonucleotide sequences of 20–200 nt, preferably 30–50 nt. Bridging oligonucleotides of 6–40 nt are designed to anneal to assembly oligonucleotides and form the nick sites on the immobilized strand. The extent of complementary overlap in the oligonucleotides forming the duplex regions may be any length so as to provide sufficient specificity and affinity. In a preferred embodiment, the complementary overlap will be 5 to 10 nt and may be up to 50 nt. The assembly and bridging oligonucleotides comprising the assembled gene are selected according to the predicted annealing properties, i.e. thermal melting temperature, $T_m$. The duplex regions resulting from annealing of the oligonucleotides must be stable enough to endure the washing step, and other manipulations, and to undergo efficient ligation.

Assembly polynucleotides may contain: (i) nucleotide units such as A, dA, C, dC, G, dG, U, T, dU, 5-methyl-C, 5-methyl-dC, I, dI, 2-amino-A, 2-amino-dA, 5-Br-U, 5-Br-dU, 5-F-U, 5-F-dU, 5-propynyl dC, 5-propynyl-dU, (ii) internucleotide linkages such as phosphodiester, phosphorothioate, N-3-phosphoramidate, and (iii) sugars such as 2'-deoxyribose, 2'-O-methyl-ribonucleotides, 2'-fluoro-ribonucleotides, and 2'-amino-ribonucleotides analogs.

Commercially available software programs may be used to design the optimal set of oligonucleotides based on energy-of-hybridization calculations resulting in a narrow range of $T_m$ values (Sambrook, 1989, p. 11.46). Further considerations for oligonucleotide sequence design are (i) avoiding self-complementary hairpin regions, (ii) avoiding poor synthesis efficiency regions, e.g. four or more consecutive G monomers, (iii) rare or poorly expressed codons, and (iv) placement of restriction sites for cleavage and further cloning operations. The entire set of oligonucleotides required to practice the assembly methods of the present invention can thus be designed and synthesized.

The immobilized double-stranded polynucleotide sequence may be a conserved, or universal sequence, and not part of the functional gene. The sequence of the immobilized fragment may contain a restriction site cleavable by a restriction enzyme. The immobilized oligonucleotide may be linked to a larger polynucleotide fragment, such as a plasmid or vector. Examples of suitable plasmids for the present invention include M13-derived vectors, pUC, and pGEM (Sambrook, 1989, Chapter 1), which can be grown and harvested from large scale bacterial culture (Berger, 1987, p. 145–70) and cut at known restriction sites for assembly of polynucleotides.

V. Amplification of Immobilized Polynucleotides on Solid-Support

Immobilized ligation products may be amplified as templates by the polymerase chain reaction (Stamm, 1995). After assembly of, e.g. 50–1000 pmole, immobilized ligation product is complete, PCR reagents may be added as a solution, including DNA polymerase, nucleotide 5' triphosphates, and two primers complementary to (i) the immobilized ligation product and (2) its complement. The temperature may be cycled between the annealing/extension and denaturation temperatures to generate double-stranded polynucleotide copies, in solution, of the immobilized ligation product. Incorporation of fluorescent dyes, as fluorescent-labelled primers or as fluorescent-nucleotides, can generate fluorescent-labelled and detectable polynucleotides. Multiple PCR products of different or the same sizes can be obtained from a single assembled polynucleotide with a plurality of primers, each complementary to different portions of the immobilized ligation product, and selected as pairs on opposing strands. When primers defining certain PCR products are labeled with different fluorescent dyes, the multiple PCR products can be spectrally discriminated, thereby detected and quantitated. Multiplex PCR on solid-support is also a convenient, efficient way to handle templates for PCR on solid-support, giving rise to less contamination from adventitious template dispersal and errant amplification.

The sequence of the immobilized ligation product can be analyzed by solid-phase Sanger dideoxy DNA sequencing methods.

VI. Detection and Quantitation of Immobilized Polynucleotides by Fluorescence

Assembled polynucleotides on solid-support of the present invention can be detected and quantitated by fluorescent-probe assays. The assays include a self-quenching oligonucleotide probe which is complementary to a portion of the immobilized ligation product. The probe includes a fluorescent reporter dye and quencher arranged to interact through a fluorescence resonance energy transfer (FRET) effect (Clegg, R., 1992). The quencher can interact with the reporter to alter its light emission, usually resulting in the decreased emission efficiency of the reporter. The efficiency of quenching diminishes with distance from the reporter to the quencher.

In the present invention, the probe may be comprised of nucleotides near the 5' terminus which are substantially complementary to the nucleotides near the 3' terminus whereby the unannealed probe exists in a quenched state. Upon annealing of the probe to the immobilized ligation product, the quenching effect is diminished and fluorescence can be detected. The increase in fluorescence of self-complementary, self-quenching probes ("Molecular Beacons") upon hybridization to target polynucleotides is sufficient for sensitive assay results (Tyagi, 1996; Tyagi, 1997).

Figure 9:
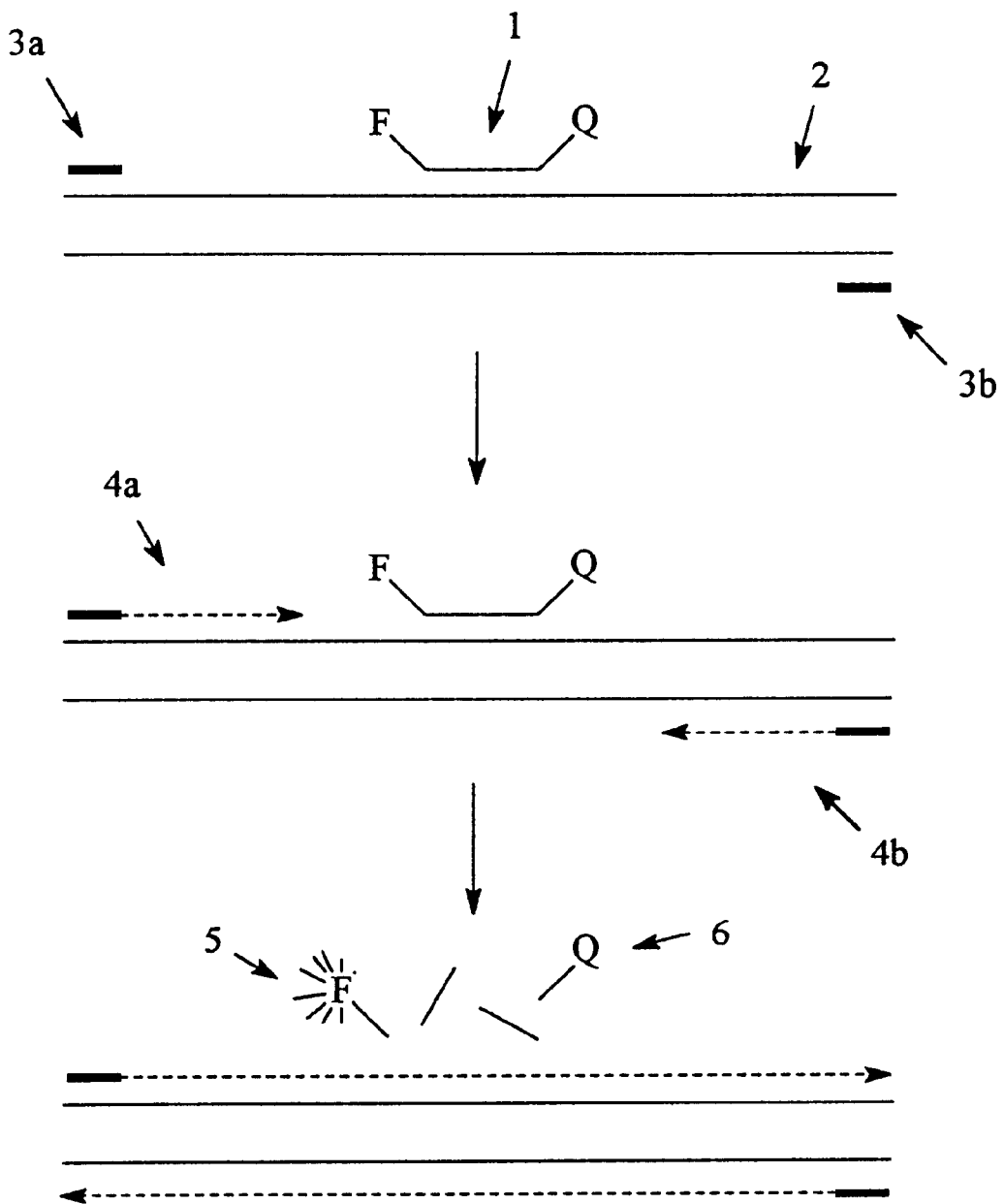
FIG. 9 shows the TaqMan® exonuclease assay whereby self-quenching probe 1, including both a reporter label, F, and a quencher label, Q, and target primers 3a and 3b are hybridized to target polynucleotide 2. During the polymerization phase of amplification, the primers 3a and 3b are extended using a polymerase enzyme thereby forming extended primers 4a and 4b, e.g., using a DNA polymerase. During the primer extension reaction, a 5'→3' nuclease activity of the polymerase serves to cut the probe 1 so as to form probe fragments, including reporter-bearing fragment 5 and quencher-bearing fragment 6. Thus, the reporter and quencher labels are separated thereby preventing energy transfer between the two and the emission of the reporter becomes unquenched upon digestion of the probe, resulting in an increase in fluorescence.

A fluorescence-based, exonuclease assay (TaqMan®) provides real time measurements of amplification products during PCR (Lee, 1993; Holland, 1991). A self-quenching fluorescence probe complementary to a site of the immobilized ligation product is included in the PCR mixture. During amplification, the probe anneals to target and is displaced and cleaved by the 5'→3' exonuclease activity of the polymerase (FIG. 9). A fluorescent signal is released that is proportional to the amount of assembled polynucleotide present (Livak 1996; Lee, 1993). The exonuclease assay gives direct detection of PCR products derived from amplification of assembled polynucleotides on solid-support with no further sample processing. As PCR proceeds, polymerase cleaves the annealed probe, separating the reporter and quencher, resulting in an increase in fluorescence.

Certain preferred embodiments of the present invention include methods for the end-point and real-time measurements of amplification product formed from the immobilized polynucleotide. In an end-point mode, the fluorescence measurement is performed after amplification of the assembled polynucleotide is complete. In a real-time mode, fluorescence measurements is performed multiple times during the amplification reaction, e.g., after each thermocycle of a PCR process. The real-time mode is preferred when a quantitative measure of assembled polynucleotide (loading of polynucleotide per gram solid-support) is required.

VII. Self-Quenching Probes

In a preferred embodiment of the self-quenching fluorescence probe, the reporter dye is separated from the quencher dye by at least 12 nucleotides, the reporter dye is attached at the 5' terminus or 3' terminus of the self-quenching fluorescence probe, and the quencher dye is attached at the 5' terminus or 3' terminus (Livak, 1998). The self-quenching probe is designed so as to bring the reporter into close proximity with the quencher so as to permit efficient energy transfer from the reporter to the quencher (Clegg, 1992; Cardullo, 1988; Livak, 1995). The reporter and quencher may also be attached to the 3' terminal nucleotide. In other embodiments of the invention, the fluorescer and quencher are attached at internal sites on the polynucleotide. The invention also includes embodiments in which one of the two fluorophores is located at an internal site and the other fluorophore is attached to a terminus of the polynucleotide.

Dyes suitable as reporters may also be suitable as quenchers. Similarly, dyes suitable as quenchers may also be suitable as reporters. In one embodiment of a self-quenching probe, 6-carboxy-fluorescein (6-FAM) is labelled at the 5' terminus of the probe as the reporter and 6-carboxytetramethylrhodamine (TAMRA) is labelled at the 3' terminus as the quencher such that the TAMRA dye substantially quenches any fluorescent emissions by 6-FAM until cleaved by polymerase.

Preferred embodiments of reporter moieties are fluorescein dyes with the general structure and numbering system below, where L is a linker.

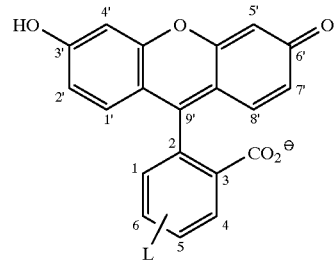

Figure 7:
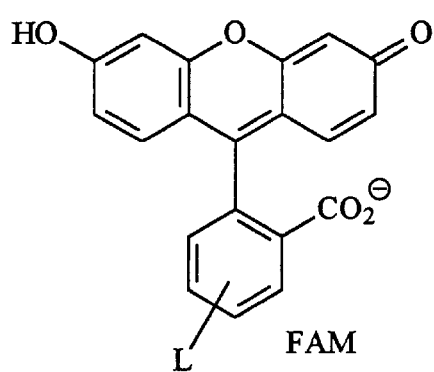
FIG. 7 shows the structures of 5-carboxyfluorescein (5-FAM), 6-carboxyfluorescein (6-FAM), 2',4',1,4,-tetrachlorofluorescein (TET), 2',4',5',7',1,4-hexachlorofluorescein (HEX), and 2',7'-dimethoxy-4',5'-dichloro-6-carboxyrhodamine (JOE) where L is a linker, and including substituted forms thereof
Figure 7:
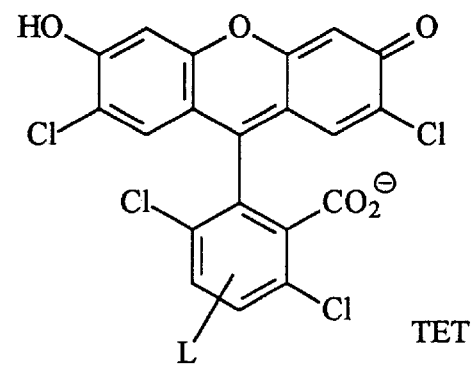
Figure 7:
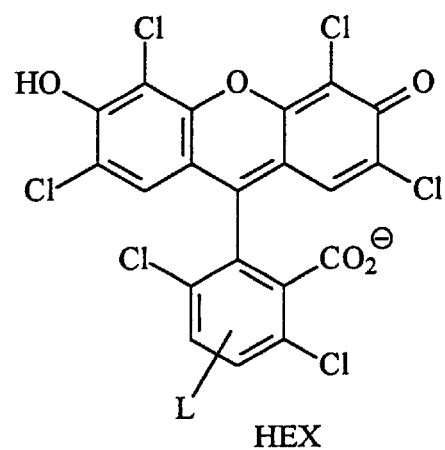
Figure 7:
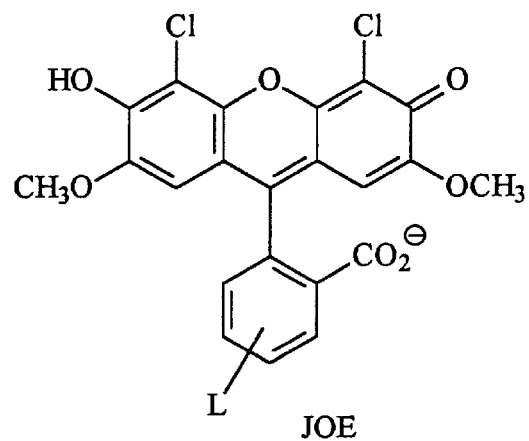

Preferred embodiments of fluorescein reporter dyes are 5-carboxyfluorescein (5-FAM), 6-carboxyfluorescein (6-FAM), 2',4',1,4,-tetrachlorofluorescein (TET), 2',4', 5',7', 1,4-hexachlorofluorescein (HEX), and 2',7'-dimethoxy-4',5'-dichloro-6-carboxyfluorescein (JOE) (FIG. 7). Other embodiments of reporter moieties are cyanine dyes, dansyl derivatives, and the like.

Figure 8:
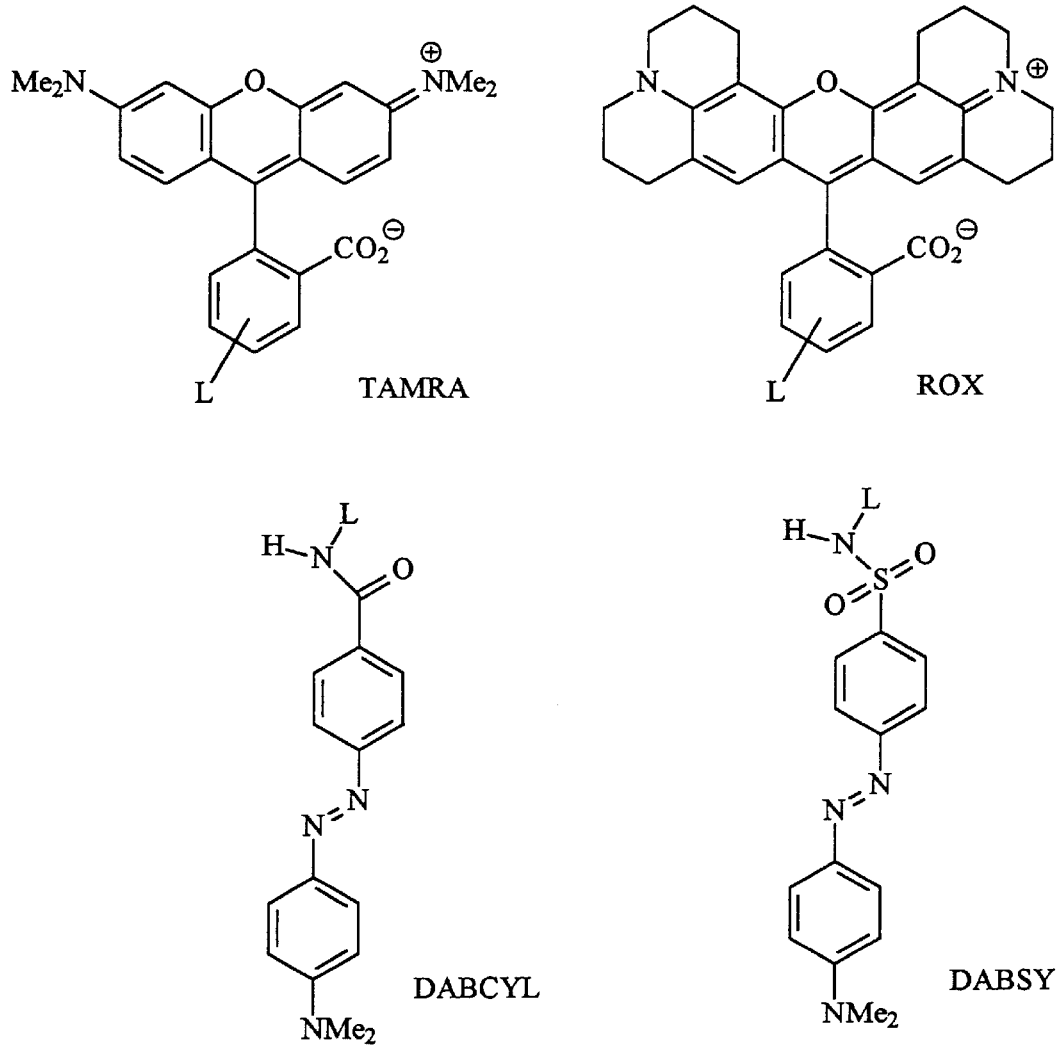
FIG. 8 shows the structures of quencher moieties tetramethyl-6-carboxyrhodamine (TAMRA), and tetrapropano-6-carboxyrhodamine (ROX), DABSYL and DABCYL, where L is a linker, and including substituted forms thereof

Preferred embodiments of quencher moieties are; (i) rhodamine dyes (Bergot, selected from the group consisting of tetramethyl-6-carboxyrhodamine (TAMRA), and tetrapropano-6-carboxyrhodamine (ROX), and (ii) DABSYL, DABCYL, cyanine, anthraquinone, nitrothiazole,and nitroimidazole compounds and the like (FIG. 8). Rhodamine dyes bear the general structure and numbering system below, where L is a linker.

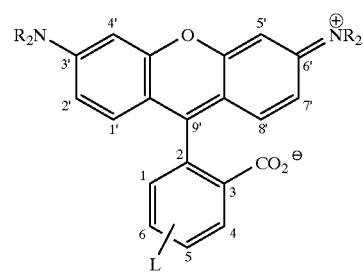

Fluorescein and rhodamine derivatives of the present invention may be substituted at one or more of the numbered positions above.

VIII. Cleavage of Polynucleotides

The assembled polynucleotide can be released from the solid-support by cleaving the linker by chemical or enzymatic means, or a combination of both. By enzymatic cleavage, the assembly and bridging oligonucleotides may be chosen to contain a restriction enzyme recognition sequence, typically of 4–8 base pairs in length, then cleavage of the assembled polynucleotide from the solid-support can occur with the appropriate restriction enzyme. For example, cleavage of the sequence, represented by the example below, within 50 pmole of an assembled polynucleotide can be conducted in a mixture of 1 unit of HindIII restriction enzyme, 10 mM Tris-HCl, 10 mM MgCl$_2$, 50 mM NaCl, 1 mM dithiothreitol, pH 7.9, at 25° C., in a total volume of 25 μl.

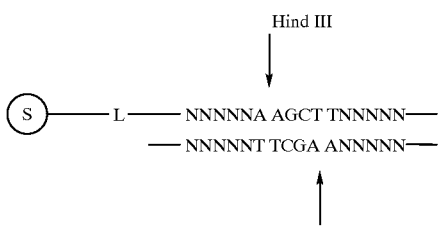

A single-stranded, assembled polynucleotide on solid-support can be cleaved by restriction enzymes by hybridizing an oligonucleotide of 6–40 nt, or longer, to a restriction site of the polynucleotide, followed by treatment with the corresponding restriction enzyme. Cleavage will occur at the double-stranded restriction site, resulting in separation of the polynucleotide from the solid-support. The sticky end of the cleaved polynucleotide will then be ready for ligation and cloning steps.

By chemical cleavage, the assembled polynucleotide may contain labile functionality that is cleavable by chemical reagents. For example, L in the figure above may be a trityl group to be cleaved with a weak acid, such as brief treatment at room temperature with acetic acid. Alternatively, L may be a base labile group such as ester or carbamate to be cleaved with ammonium hydroxide, sodium hydroxide, or other aqueous reagents at or about pH 12. The linker L may be a disulfide functional group cleavable by mild reducing agents such as dithiothreitol (Cleland's reagent). The linker L may be a silyl ether functional group cleavable by fluoride ion with reagents such as tetrabutylammonium fluoride. Typical conditions of an ester linkage of an assembled polynucleotide on solid-support would include treating about 1 mg of support with 100 μl of concentrated ammonium hydroxide at 25° C. for 6 hours and withdrawing the supernatant to a separate vessel for removal of the ammonia and water under vacuum.

X. Automation of Assembly

A device may be constructed to synthesize a polynucleotide on a solid-support by automating the steps of annealing, ligation, and primer extension in a cyclical manner according to the present invention. Liquid reagents can be delivered from vessels to the solid-supports under microprocessor control according to a program. Applying the methods of the present invention, particularly the enzymatic means of polynucleotide assembly to solid-support chemistry, takes advantage of the convenience and efficiency realized by other chemical, solid-phase biopolymer and small molecule synthesis methods. Temperature control can be realized by immersing the reaction vessels in cooling or heating fluids, or placement in cooling/heating zones, e.g. heating blocks, ovens, chillers. All steps of the assembly process and thermal cycling during PCR can be conducted between 0–100° C. The heterogeneous reactions of the present invention, whereby liquid reagents are delivered to an immobilized reactant on a stationary solid-phase, can exhibit rapid kinetics and high yields while obviating the need for product work-up, isolation, and purification. Thus, iterative processes, such as monomer additions in assembling biopolymers, is well suited for solid-support synthesis, by manual and automated means. The present invention lends itself to automation of high-throughput, parallel synthesis of genes.

Arrays, addressable locations on a surface to which reagents, detection elements, or devices can be located, can be utilized with the present invention. Typically the array is a planar surface with locations fixed in a format within a device by which automated means can visit repeatedly for the purposes of (i) conducting chemical or enzymatic reactions, (ii) detecting changes or interactions, or (iii) fixing or mounting for display a multitude of samples. The spatial arrangement of the synthesis array may be a two-dimensional surface addressable by a programmed, robotic automated liquid delivery apparatus.

All publications and patent applications are herein incorporated by reference to the same extent as if each individual publication or patent application was specifically and individually indicated to be incorporated by reference.

Although only a few embodiments have been described in detail above, those having ordinary skill in the molecular biology art will clearly understand that many modifications are possible in the preferred embodiment without departing from the teachings thereof All such modifications are intended to be encompassed within the following claims.

We claim:

1. A method of synthesizing a polynucleotide on a solid-support, the method comprising the steps of:
   a. annealing one or more bridging oligonucleotides and two or more assembly oligonucleotides such that a ligatable nick site is formed between adjacent assembly oligonucleotides, wherein one of the assembly oligonucleotides is immobilized to a solid support;
   b. ligating the ligatable nick sites thereby forming an immobilized ligation product;
   c. annealing a primer to the immobilized ligation product; and
   d. extending the primer to create an immobilized, double-stranded polynucleotide.

2. The method claim 1 wherein steps a. and b. are repeated a plurality of cycles.

3. The method claim 1 wherein steps a. and b. are repeated from 1 to 100 cycles.

4. The method of claim 1 wherein the solid support is comprised of small particles, beads, membranes, frits, non-porous surfaces, addressable arrays, vectors, plasmids, or polynucleotide-immobilizing media.

5. The method of claim 1 to synthesize a polynucleotide of length between 50 and 5000 nucleotide base pairs.

6. The method of claim 1 wherein the assembly oligonucleotides are 20–200 nucleotides in length and the bridging oligonucleotides are 6–40 nucleotides in length.

7. The method of claim 1 wherein step d. of extending the primer annealed to the immobilized ligation product comprises nucleotide 5' triphosphates selected from the group consisting of;

ATP, dATP, CTP, dCTP, GTP, dGTP, UTP, TTP, dUTP, 5-methyl-CTP, 5-methyl-dCTP, ITP, dITP, 2-amino-ATP, 2-amino-dATP, 5-Br-UTP, 5-Br-dUTP, 5-F-UTP, 5-F-dUTP, 5-propynyl dCTP, 5-propynyl-dUTP and;

the corresponding α-thiotriphosphates, 2'-O-methyl-ribonucleotide triphosphates, 2'-fluoro-NTP, 2'-amino-NTP analogs, and fluorescent labelled-NTP.

8. The method of claim 7 wherein said fluorescent labels are attached at the N-9 or C-8 positions of the purine or deazapurine, and the C-5 position of the pyrimidine and are selected from the group consisting of FAM, TET, HEX or JOE.

9. The method of claim 1 wherein said assembly and bridging oligonucleotides are comprised of;

A, dA, C, dC, G, dG, U, T, dU, 5-methyl-C, 5-methyl-dC, I, dI, 2-amino-A, 2-amino-dA, 5-Br-U, 5-Br-dU, 5-F-U, 5-F-dU, 5-propynyl dC, 5-propynyl-dU and;

the corresponding phosphorothioate, N-3-phosphoramidate, 2'-O-methyl-ribonucleotides, 2'-fluoro-ribonucleotides, and 2'-amino-ribonucleotides analogs.

10. The method of claim 1 further comprising the step of periodic washing under non-denaturing conditions after steps a. and b.

11. The method of claim 1 further comprising the steps of washing the support under denaturing conditions after each ligation step b.

12. The method of claim 11 wherein the denaturants are selected from the group consisting of sodium hydroxide, ammonium hydroxide, formamide, urea, sodium chloride and sodium acetate.

13. The method of claim 1 wherein the polynucleotide is cleaved from the support by chemical cleavage.

14. The method of claim 1 wherein the polynucleotide is cleaved from the support by enzymatic cleavage.

15. The method of claim 1 further comprising the step of annealing a self-quenching, fluorescence probe complementary to said immobilized polynucleotide.

16. The method of claim 15 wherein said self-quenching, fluorescence probe is comprised of nucleotides near the 5' terminus substantially complementary to the nucleotides near the 3' terminus whereby the unannealed probe exists in a quenched state.

17. The method of claim 15 wherein annealing of the self-quenching, fluorescence probe to the immobilized double-stranded polynucleotide is measured by fluorescence detection.

18. The method of claim 1 wherein step d. of extending the primer annealed to the immobilized ligation product is a polymerase chain reaction comprised of;

a thermal-stable nucleic acid polymerase having 5'→3' nuclease activity, said primer complementary to the immobilized ligation product, a second primer complementary to the complement of the immobilized ligation product, 5' nucleotide triphosphates; and a self-quenching fluorescence probe, said probe existing in at least one single-stranded conformation when unannealed to polynucleotide wherein a quencher quenches the fluorescence of a reporter and at least one conformation when annealed to said immobilized ligation product, wherein the fluorescence of the reporter is unquenched; and the steps of annealing said primers to said immobilized ligation product;

amplifying the immobilized ligation product by PCR, whereby target polynucleotide amplification products are produced.

19. The method of claim 18 wherein said nucleic acid polymerase digests said self-quenching, fluorescence probe during amplification to separate said reporter from said quencher.

20. The method of claim 18 wherein the target polynucleotide amplification products are measured by fluorescence detection.

21. The method of claim 18 wherein the target polynucleotide amplification products are measured and quantitated by end-point analysis.

22. The method of claim 18 wherein the target polynucleotide amplification products are measured and quantitated by real-time analysis.

* * * * *

UNITED STATES PATENT AND TRADEMARK OFFICE
CERTIFICATE OF CORRECTION

PATENT NO.: 5,942,609

DATED: August 24, 1999

INVENTOR(S): Michael W. Hunkapiller and Andrew C. Hiatt

It is certified that error appears in the above-identified patent and that said Letters Patent is hereby corrected as shown below:

On the title page, item:

[73] Assignee: "The Porkin-Elmer Corporation" should read --The Perkin-Elmer Corporation--.

Signed and Sealed this

Twenty-fifth Day of January, 2000

Attest:

*Attesting Officer*

*Acting Commissioner of Patents and Trademarks*